(12) United States Patent
Gabele et al.

(10) Patent No.: US 11,701,135 B2
(45) Date of Patent: Jul. 18, 2023

(54) MEDICAL INSTRUMENT WITH CLEANING GAP IN THE CLOSURE REGION

(71) Applicant: Karl Leibinger Medizintechnik GmbH & Co. KG, Mühlheim (DE)

(72) Inventors: Lorenz Gabele, Mühlheim (DE); Jürgen Rometsch, Mühlheim (DE); Volker Scheu, Mühlheim (DE); Oliver Schulz, Mühlheim (DE)

(73) Assignee: Karl Leibinger Medizintechnik GmbH & Co. KG, Mühlheim (DE)

( * ) Notice: Subject to any disclaimer, the term of this patent is extended or adjusted under 35 U.S.C. 154(b) by 921 days.

(21) Appl. No.: 16/324,931

(22) PCT Filed: Sep. 6, 2017

(86) PCT No.: PCT/EP2017/072329
§ 371 (c)(1),
(2) Date: Feb. 12, 2019

(87) PCT Pub. No.: WO2018/046534
PCT Pub. Date: Mar. 15, 2018

(65) Prior Publication Data
US 2021/0275202 A1    Sep. 9, 2021

(30) Foreign Application Priority Data

Sep. 6, 2016    (DE) .......................... 102016116624.3

(51) Int. Cl.
*A61B 17/28* (2006.01)
*A61B 90/00* (2016.01)

(52) U.S. Cl.
CPC .......... *A61B 17/2816* (2013.01); *A61B 17/28* (2013.01); *A61B 2090/0813* (2016.02)

(58) Field of Classification Search
CPC ........ A61B 17/2816; A61B 2090/0813; A61B 17/28
See application file for complete search history.

(56) References Cited

U.S. PATENT DOCUMENTS

| 1,973,569 A | 9/1934 | Kurtz |
| 2,632,661 A * | 3/1953 | Cristofv ............. A61B 17/2816 606/208 |

(Continued)

FOREIGN PATENT DOCUMENTS

| DE | 202009014310 U1 | 3/2010 |
| DE | 202010010843 U1 | 12/2010 |

(Continued)

OTHER PUBLICATIONS

Nov. 30, 2020—(RU) Substantive Examination Office Action and Search Report—App 2019102784—machine English translation.

(Continued)

*Primary Examiner* — Timothy J Neal
*Assistant Examiner* — Mitchell Brian Hoag
(74) *Attorney, Agent, or Firm* — Banner & Witcoff, Ltd.

(57) ABSTRACT

A medical instrument includes a first hand lever which has a manually actuated grip portion at its proximal end, a work portion for gripping, clamping or cutting an object at its distal end, and, lying between these, a bearing portion on which a bearing element engages in order to permit pivotability about a rotation axis between the first hand lever and a second hand lever, wherein the second hand lever has a grip portion at its proximal end, a work portion at its distal end, and, lying between these, a guide portion on which the bearing element engages, wherein the guide portion of the second hand lever has on one side a recess for receiving the bearing portion of the first hand lever such that two guide protrusions located distally and proximally of the recess at (Continued)

least partially cover the bearing portion in an operating position.

12 Claims, 9 Drawing Sheets

(56) References Cited

U.S. PATENT DOCUMENTS

| | | | | |
|---|---|---|---|---|
| 3,459,187 | A * | 8/1969 | Pallotta | A61B 17/2816 30/267 |
| 9,662,130 | B2 | 5/2017 | Bartels et al. | |
| 2007/0276431 | A1* | 11/2007 | Swartz | A61B 17/2816 606/208 |
| 2008/0004650 | A1* | 1/2008 | George | B26B 13/08 606/174 |
| 2012/0029554 | A1* | 2/2012 | Kreidler | B25B 7/08 606/205 |
| 2015/0245877 | A1 | 9/2015 | Tontarra et al. | |
| 2017/0119416 | A1* | 5/2017 | Sajid | A61C 3/14 |
| 2018/0000536 | A1* | 1/2018 | Becker | A61B 18/1445 |
| 2019/0150965 | A1* | 5/2019 | Barthelmes | A61B 17/2816 |
| 2019/0336156 | A1* | 11/2019 | Hammerland, III | A61B 17/29 |
| 2020/0197034 | A1* | 6/2020 | Ettwein | A61B 17/2816 |
| 2020/0383695 | A1* | 12/2020 | Weisshaupt | A61B 17/2816 |

FOREIGN PATENT DOCUMENTS

| | | |
|---|---|---|
| DE | 202011107977 U1 | 11/2011 |
| DE | 202013010321 U1 | 1/2014 |
| JP | S58174064 U | 11/1983 |
| JP | H04224785 A | 8/1992 |
| JP | H0780164 A | 3/1995 |
| RU | 2013148076 A | 4/2012 |
| WO | 2017031506 A1 | 2/2017 |

OTHER PUBLICATIONS

Nov. 24, 1937—Beiliage zur Geschichte der Medizinmechanik. p. 239-242.
Oct. 26, 2017—International Search Report and Written Opinion of PCT/EP2017/072329.
Jun. 27, 2017—German Search Report of 102016116624.3.

* cited by examiner

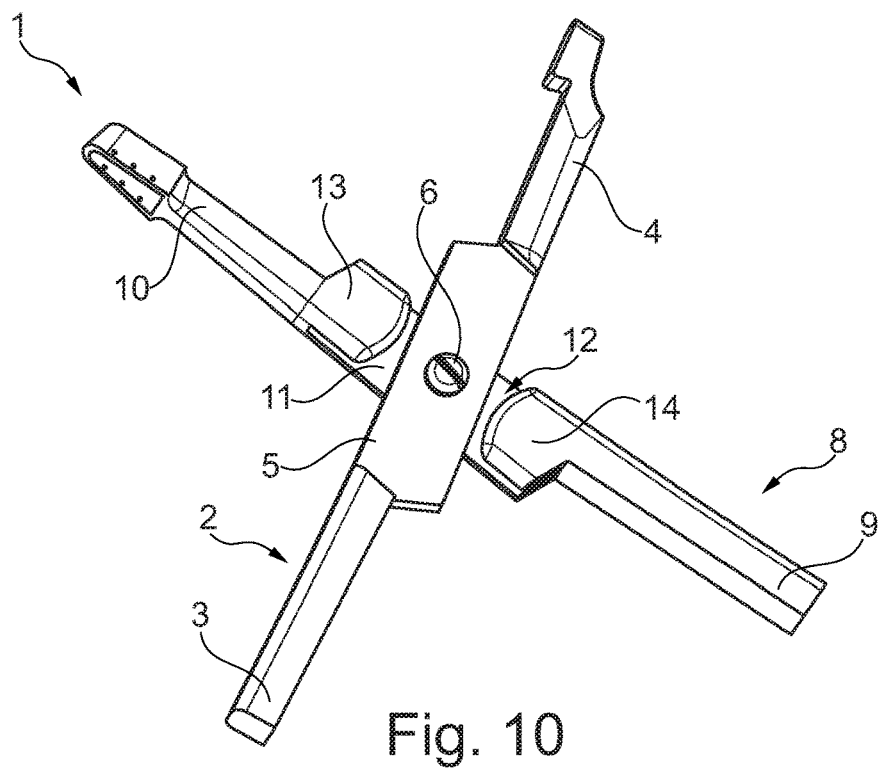
Fig. 10
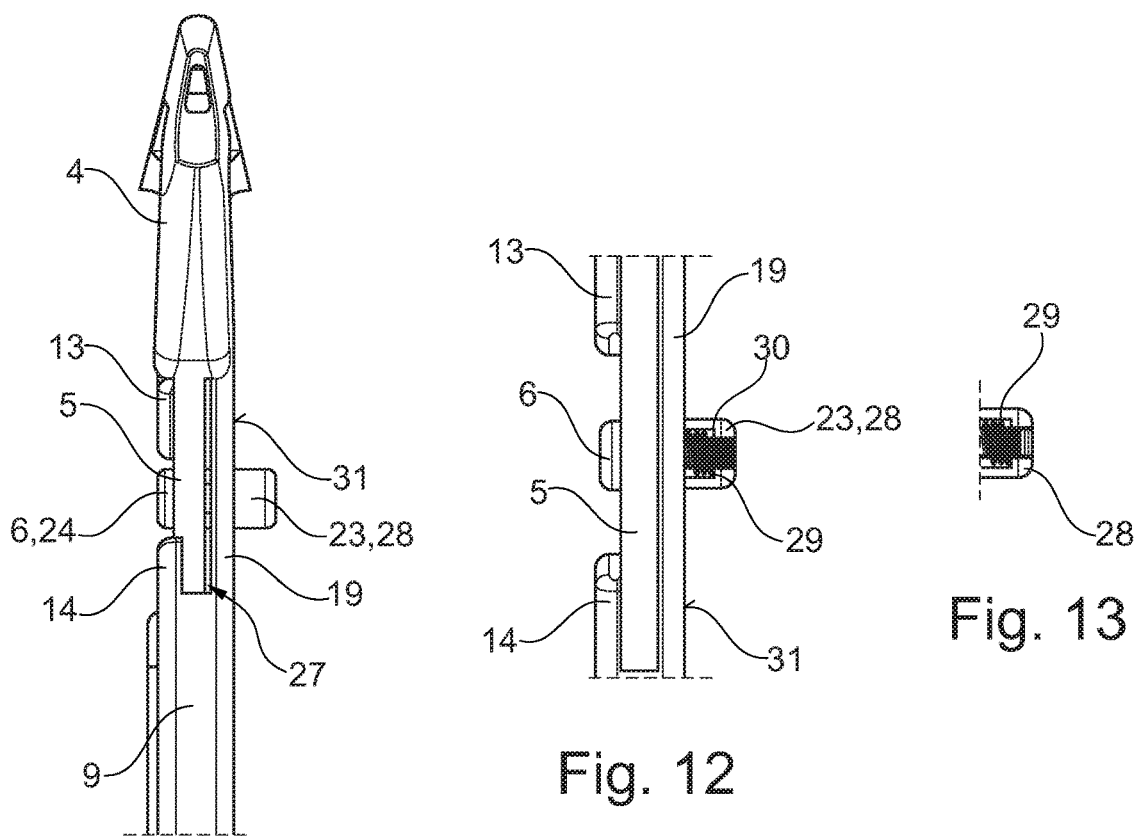
Fig. 11
Fig. 12
Fig. 13

MEDICAL INSTRUMENT WITH CLEANING GAP IN THE CLOSURE REGION

CROSS-REFERENCE TO RELATED APPLICATIONS

This application is a U.S. National Stage application under 35 U.S.C. § 371 of International Application PCT/EP2017/072329, published as WO2018/046534, filed Sep. 6, 2017, which claims the benefit of priority to German Patent Application DE 10 2016 116 624.3, filed Sep. 6, 2016. Benefit of the filing date of each of these prior applications is hereby claimed. Each of these prior applications is hereby incorporated by reference in its entirety.

The present invention relates to a medical instrument and, resp., a hand tool such as a clamp, forceps or any other scissors-type hand tool, comprising a first hand lever which has a grip portion provided for manual actuation at its proximal end, a work portion e.g. in the form of a branch, for gripping, clamping or cutting an object at its distal end and, lying between these, a bearing portion on which a bearing element engages so as to permit pivotability about a rotation axis between the first hand lever and a second hand lever, wherein the second hand lever has a grip portion at its proximal end, a work portion at its distal end and, lying therebetween, a guide portion on which the bearing element engages, wherein the guide portion of the second hand lever on one side has an insertion recess for receiving the bearing portion of the first hand lever so that two guide protrusions located distally and proximally of the insertion recess at least in portions cover the bearing portion in an operating position in which gripping, clamping or cutting takes place.

From DE 20 2013 010 321 U1, a forceps-type medical instrument is known which consists of a first hand lever including a guide plate and a second hand lever including a bearing plate which are pivotally connected to each other via a bearing journal arranged in the area of the guide plate and the bearing plate and provided with a radially expanded head part, the bearing plate forming in each of its edge portions at the longitudinal sides a receiving groove in which the guide plate engages in its operating position, wherein the bearing plate includes, between the receiving grooves, an recess extending over the complete width of the bearing plate and the guide plate is rotatable relative to the bearing plate from its operating position into a cleaning position in which the guide plate is going to overlap the recess and in the area of the recess between the guide plate and the bearing plate a spacer is provided the height of which in the direction of the bearing journal is equal to or smaller than the depth of the recess.

DE 20 2010 010 843 U1 discloses a scissors-type or forceps-type medical hand tool with two hand levers each having two arms which in the area of two central portions flattened in plate shape are articulated to each other by a pivot pin and are pivoting against each other, wherein a preferably short lever arm of each hand lever is in the form of a tool and the respective second longer lever arm is in the form of a grip, wherein the pivot pin immovably fixed in the flattened central portion of the one hand lever is provided with an annular flange which has a distance corresponding to at least twice the thickness of the central portion of the second hand lever supported on the pivot pin from the central portion of the first hand lever in which the pivot pin is fixed so that the second hand lever in the maximum pivoting position of the two hand levers on the pivot pin is movable at least so far into a position in which also the opposed inner surfaces of the flattened central portions and the pivot pin are exposed.

DE 20 2011 107 977 U1 in turn discloses a scissors-type or forceps-type medical instrument with first and second hand levers each of which has a grip member and a tool member and which are pivoted to each other via a bearing journal provided with a radially expanded head piece, wherein the first hand lever forms a guide plate in the area between its grip member and its tool member and the second hand lever in the area forms, between its grip member and its tool member, a bearing plate in the area of which the bearing journal is fixedly arranged, wherein the guide plate has a breakthrough for pivotally receiving the bearing journal and wherein, in the normal operating condition of the instrument, the guide plate and the bearing plate contact their full surfaces, the breakthrough of the guide plate being in the form of a slotted hole extending in the longitudinal direction of the guide plate and the slotted hole having in the edge area of its end portion adjacent to the tool part a first expanded recess and having in the edge area of its end portion opposite in the longitudinal direction a second expanded recess in which the head piece of the bearing journal optionally can be received and the first recess has a smaller depth than the second recess and the bearing plate on its contact surface facing the guide plate has a transverse groove disposed in the area of the bearing journal and extending transversely to the bearing plate, with the depth thereof corresponding at least to the depth of the first recess of the slotted hole and the width thereof corresponding at least to the width of the guide plate, and wherein the first hand lever can be brought with its guide plate into a pivoting position aligned with the transverse groove and is adjustable in the direction of the bearing journal into the transverse groove so far that the head piece of the bearing journal is disengaged from the first recess of the slotted hole and the head piece of the bearing journal can be made to overlap, by adjusting the second hand lever, the second recess of the slotted hole with its bearing plate and the bearing journal along the slotted hole and can be made to engage, by adjustment in the direction of the bearing journal, in the second recess and the guide plate and the bearing plate in this position are spaced from each other.

Close prior art is also known from the documents JP H04224785 A, JP H0780164 A and JP S58174064 U. In addition, the article by R. Ulrich "Über die Entwicklung zerlegbarer Klemmen-und Zangenschlüsse"[1] from "Die Medizinmechanik"[2] vol. 58, 1937, no 24, pp. 239-242 is known.

[1] "The development of dismountable clamp and forceps closures"
[2] "Medical Mechanics"

In the medical instruments known from prior art the guide portions are configured to be very minimal, however, so that exact and precise guiding of the two hand levers relative to each other is not always ensured. Moreover, in some of the known medical instruments the mounting and, resp., dismounting of the medical instrument is connected with major efforts.

It is the object of the invention to avoid or at least alleviate the drawbacks from the state of the art and especially realize spacing of the two hand levers in the operating position so as to enable or, resp., facilitate draining of fluids such as e.g. ichor, blood etc. already during use. This also permits facilitated cleaning and/or sterilization of the medical instrument.

The object of the invention is achieved in a generic medical instrument by the fact that the bearing portion of the first hand lever is pressed, by means of a spacing element that provides distance through force or resistance, away from the guide portion of the second hand lever in the operating position such that a cleaning gap between the first hand lever and the second hand lever extends into the area beneath the guide protrusions on the side of the first hand lever facing away from the guide protrusions, preferably along the entire length of the guide portion.

Advantageous embodiments are claimed in the subclaims and shall be explained hereinafter.

Hence, it is of advantage when the spacing element is in the form of a separate or integral component. A separate component offers the advantage of being adapted to be easily replaced, whereas an integrally formed component reduces the total number of components and facilitates assembly.

It has turned out to be advantageous when the spacing element is configured as a ring, as a collar or as one or more land(s).

Another advantageous embodiment provides that the spacing element is in the form of a spring, a magnet or a pressure tank or includes a thermally active element. Here the space between the guide portion and the bearing portion is formed by the spacing element applying force which spaces the bearing portion apart from the guide portion.

It is especially advantageous when the spacing element is configured so that a cleaning gap height is (systematically) manually adjustable. Said spacing element enables the user of the medical instrument to individually adapt the cleaning gap height in a variable manner.

A possible advantageous embodiment provides that the bearing element is in the form of a screw or a rivet, with a screw being more easily (and non-destructively) dismountable as compared to a rivet, whereas a rivet cannot inadvertently come loose. However, also other positive, non-positive or adhesive connections are imaginable.

It is further advantageous when the cleaning gap height in the operating position is smaller than the cleaning gap height in a cleaning position. An enlarged gap height in the cleaning position thus helps to further facilitate cleaning and sterilization of the medical instrument, while in the operating position the smaller cleaning gap height helps to further permit exact and precise guiding of the two hand levers relative to each other.

Here it is of advantage when the cleaning position corresponds to a mounting position of the two hand levers. Thus, the medical instrument can also be dismounted for cleaning and/or sterilization, as needed.

It has turned out to be advantageous for the medical instrument when the pivotability of the two hand levers relative to each other is limited by a stop mechanism which is disposed/provided preferably at the proximal end of the respective grip portion. This helps to prevent the medical instrument from being inadvertently brought into the cleaning position during use by an operator such as a physician, an operating surgeon or any other operator.

A possible exemplary embodiment provides that the work portion of the first hand lever and the work portion of the second hand lever are configured identically or differently. This depends on the purpose for which the medical instrument is intended to be used.

Furthermore, it is of advantage when the grip portions are shaped ergonomically. An ergonomic shape is understood to be such that the grip portions are shaped so that they facilitate gripping, holding and operating the medical instrument by means of one hand of an operator and, resp., render the same more comfortable for the operator, and thus easier and longer operation of the medical instrument is possible as compared to a non-ergonomic shape, such as e.g. when the grip portions are just in the form of a rod, without any curvature and having a constant thickness. Ergonomic shapes may comprise e.g. curvatures and/or recesses based on the shape/contour of a hand and/or of fingers when they are gripping/holding/operating the medical instrument.

In addition, it has turned out to be advantageous when outer edges of both guide protrusions extending in the longitudinal direction have at least one fifth of the length of the insertion recess. It is additionally of advantage when the length of the insertion recess is larger than the width of the first hand lever in the area of the bearing element. Thus, the guide protrusions help to permit proper and precise guiding of the bearing portion in the operating position, while at the same time in the cleaning and, resp., mounting position easy cleaning and, resp., mounting/dismounting can take place.

Another exemplary embodiment provides the bearing portion of the first hand lever to slidingly touch/contact the guide protrusions in an operating position and thus to be precisely guided.

Here it has turned out to be advantageous when the thickness of the bearing portion is smaller than the height of a guiding gap formed between an inner surface of the guide protrusions and the surface of a connecting arm of the guide portion facing the former. In this way, the bearing portion is precisely guided within said guiding gap and the involved relative movement of the two hand levers in the operating position can be exactly carried out.

Alternatively, it is also imaginable that the invention additionally or instead comprises one or more of the following aspects. Said aspects can be further pursued in one or more divisional applications even without the features of the independent claim.

Another advantageous embodiment of the invention thus provides, for example, that the bearing portion, approximately in the respective center, has a smaller thickness than the grip portion and/or the work portion, approximately in the respective center thereof. This is reasonable especially in terms of manufacture, as in this way the blank of the medical instrument can be manufactured with a constant thickness and in a subsequent step, for example by means of milling or any other material-abrading method, the bearing portion can be brought to the desired thickness, wherein optionally (depending on the selected method) the surface nature required for the guiding in the guiding gaps simultaneously can be produced.

It is further advantageous when the pivotability about the rotation axis allows a relative pivoting angle between the work portions from 0° to more than 90°, preferably up to 120°. This enables the medical instrument to be brought also into a cleaning position intended for cleaning and sterilization of the medical instrument. The cleaning position preferably corresponds to a mounting position in which the two hand levers are pivoted relative to each other by means of the bearing element.

Moreover, it has turned out to be advantageous when the bearing portion and the guide portion have contact surfaces facing each other which slidingly touch/contact each other in the operating position and thus precise guiding of the hand levers relative to each other is realized.

It is further advantageous to the medical instrument when the hand levers can be brought both to the operating position and to a cleaning position. The cleaning position advantageously corresponds to the mounting position in which the two hand levers are connected to each other by means of the bearing element.

In addition, it is of advantage when the guide protrusions together with the contact surface of the guide portion of the second hand lever form an undercut e.g. in the form of a guiding groove.

It is of further advantage when each of the two guide protrusions has a thickness corresponding to between about 80% and about 120% of the thickness of the bearing portion to be received in the insertion recess, and to preferably (exactly) 100%. This allows to ensure that the guide protrusions have sufficiently high stability to guide the bearing portion in an appropriately precise manner.

Another advantageous embodiment intends the guide protrusions to have, on both sides of the insertion recess, edges/rims facing each other which take a convex or spherical or rounded shape. This helps to avoid sharp edges, corners (e.g. by a projecting ridge) and thus to reduce the risk of injury for both the operator and the patient.

It is beneficial to guiding the bearing portion when the proximal guide protrusion has a proximal terminal edge which is aligned in parallel to a proximal terminal edge of the connecting arm and perpendicularly to the longitudinal axis of the second hand lever.

For the same reasons, it is of advantage when the distal guide protrusion has a distal terminal edge which is aligned in parallel to a distal terminal edge of the connecting arm and perpendicularly to the longitudinal axis of the second hand lever.

It has turned out to be advantageous when the inertia center of gravity of an area of the guide protrusion is located on the axis of symmetry extending in the longitudinal direction. This facilitates proper operability of the medical instrument.

Another possible embodiment relates to a medical instrument comprising a first hand lever which has a manually actuated grip portion at its proximal end, a work portion for gripping, clamping or cutting an object at its distal end, and, lying between these, a bearing portion on which a bearing element engages in order to permit pivotability about a rotation axis between the first hand lever and a second hand lever, wherein the second hand lever has a grip portion at its proximal end, a work portion at its distal end and, lying between these, a guide portion on which the bearing element engages, wherein a bearing is configured so that in an operating position the two hand levers are supported positively though pivotally relative to each other by means of the bearing element, and that the hand levers can be dismounted in a cleaning position without the use of tools.

A further advantageous embodiment provides for a bearing of the two hand levers relative to each other being configured in the form of a bayonet lock. This facilitates mounting as well as dismounting without the use of tools. The range in which the bayonet lock is closed, i.e. the two hand levers are in form fit with each other, corresponds to the operating position.

For this purpose, it has proven beneficial when in the bearing portion of the first hand lever the bearing element is integrally provided. This, on the one hand, facilitates mounting and, on the other hand, reduces the total number of components.

It is of further advantage when the bearing element is substantially round, i.e. circular in the pivoting plane (the plane perpendicular to the rotation axis) and in the circumferential direction preferably has equally spread, 2, 3, 4, 5 or 6 projections/protrusions. They serve for the positive connection in the form of a bayonet lock of the first hand lever to the second hand lever.

To this end, it is of advantage when the guide portion of the second hand lever is substantially round, i.e. circular in the pivoting plane (the plate perpendicular to the rotation axis) and includes a guiding gap extending in the circumferential direction. The projections of the bearing element integrated in the first hand lever engage in said guiding gap and, resp., interact with the same and thus form a bayonet-type lock.

Another advantageous embodiment provides that the peripheral guiding gap is interrupted by plural recesses preferably equally spread in the circumferential direction. The projections of the bearing element may be inserted into said recesses, i.e. the medical instrument is in the cleaning or, resp., mounting/dismounting position when the projections are positioned within the recesses.

It is of advantage when the number and the position along the periphery of the respective projections/protrusions corresponds to the number and the position along the periphery of the respective recesses. Only in this way is easy mounting and, resp., dismounting of the medical instrument possible.

Another possible embodiment provides for the bearing element being configured in the form of a pin extending along the rotation axis, wherein the guide portion of the second hand lever on one side has the insertion recess for receiving the bearing portion of the first hand lever so that the two guide protrusions located distally and proximally of the recess at least partially cover the bearing portion in the operating position in which gripping, clamping or cutting takes place. For realizing the pivoting connection of the first hand lever to the second hand lever it has proven advantageous when the bearing portion of the first hand lever includes a hole into/through which the pin can be inserted.

Advantageous embodiments of the projections/protrusions comprise e.g. the trapezoidal or pin-shaped configuration thereof. However, also any other geometric shapes are imaginable.

It is further advantageous when the pivoting of the two hand levers relative to each other in the operating position is defined by the number and the positioning of the recesses spread along the periphery.

In other words, the invention consists in the fact that a cleaning gap between the first hand lever and the second hand lever, especially provided for cleaning and/or sterilization of the medical instrument, is formed already in the operating position and extends along the entire length of the guide portion.

Hereinafter, the invention will be explained in detail by way of figures in which different embodiments are depicted, wherein:

FIG. 10 shows a top view of the medical instrument in a fifth exemplary embodiment;

FIG. 11 shows a side view of the medical instrument of the fifth exemplary embodiment;

FIG. 12 shows a cutout enlarged view of the medical instrument of the fifth embodiment in the area of the joint of the first hand lever and the second hand lever in a first position;

FIG. 13 shows a detailed view of the bearing element in a second possible position;

The figures are merely schematic and only serve for the comprehension of the invention. Like elements are provided with like reference numerals.

Features of the individual exemplary embodiments may also be realized in other exemplary embodiments. Hence, they are interchangeable.

Figure 1:
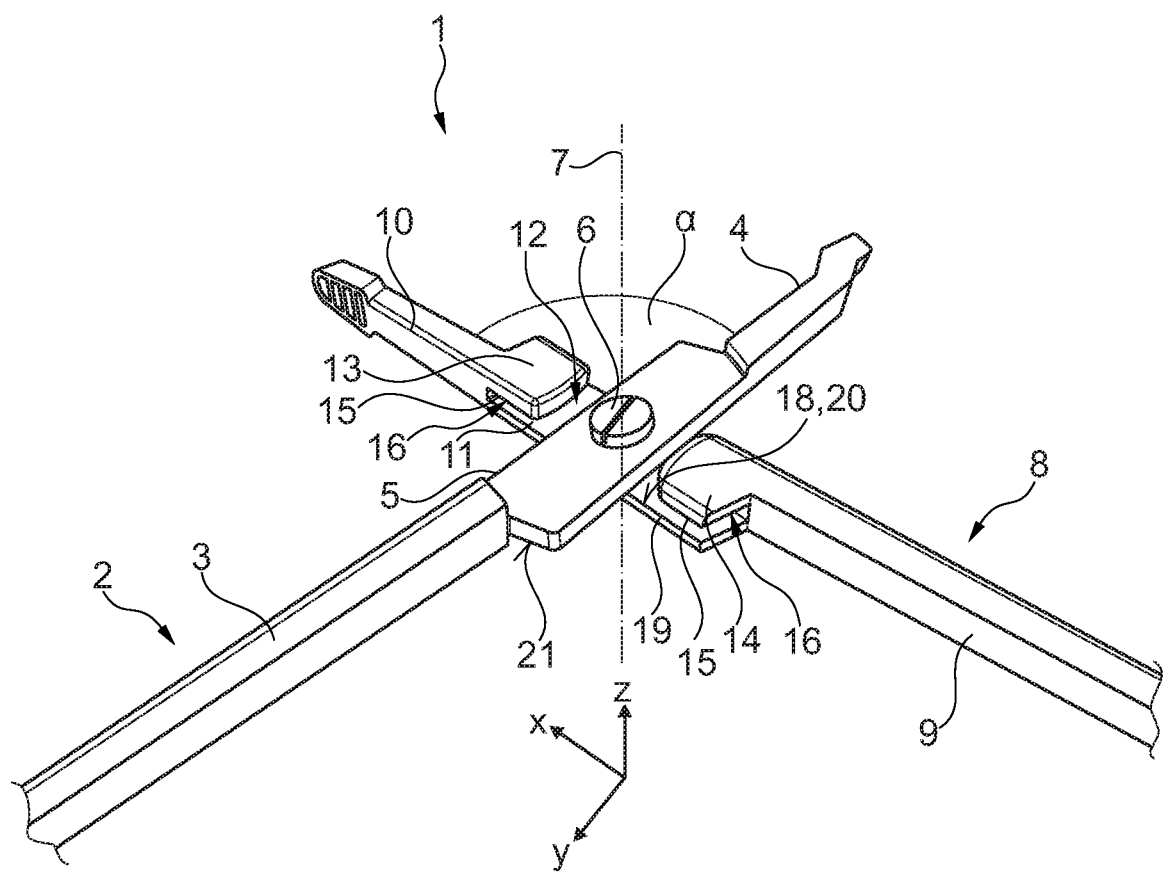
FIG. 1 shows a perspective view of a medical instrument of a first exemplary embodiment in a mounting and, resp., cleaning position.

FIG. 1 shows a medical instrument 1 of a first exemplary embodiment in a perspective view which comprises a first hand lever 2 substantially made up of three portions: a grip portion 3, a work portion 4 and a bearing portion 5.

The grip portion 3 is located at a proximal end of the first hand lever 2 and serves for manual actuation by a user such as a surgeon or operating surgeon or physician. The work portion 4 is approximately in the form of a branch and serves for gripping, clamping or cutting an object such as e.g. tissue of a patient, and is located at a distal end of the first hand lever 2. Between the grip portion 3 and the work portion 4 the bearing portion 5 is located which substantially serves for connecting the first hand lever 2 by means of a bearing element 6 to a second hand lever 8 pivotably about a joint rotation axis 7.

The second hand lever 8 comprises a grip portion 9, a work portion 10 and a guide portion 11. The grip portion 9 is located, analogously to the grip portion 3 of the first hand lever 2, at a proximal end of the second hand lever 8, and the work portion 10 is located at a distal end of the second hand lever 8. The guide portion 11 is arranged between the grip portion 9 and the work portion 10.

The guide portion 11 on one side has an insertion recess 12 which enables the bearing portion 5 to be easily mountable in a cleaning and, resp., mounting position (as shown in FIG. 1) and to cover the bearing portion 5 in a working or operating position (see FIG. 2) at least in portions by means of two guide protrusions 13, 14 which are located distally and proximally of the insertion recess 12 and thus to guide the first hand lever 2 vis-à-vis the second hand lever 8.

The mounting and, resp., cleaning position corresponds to such position in which a relative pivoting angle α, measured between the two work portions 4, 10, is selected so that the bearing portion 5 is not engaged in the guide protrusions 13, 14 and, resp., is not covered by the latter. This corresponds to such position of the two hand levers 2, 8 relative to each other that the first hand lever 2 can be easily connected to or, resp., mounted on the second hand lever 8 with the aid of a bearing element 6 in the area of the bearing portion 5.

Figure 2:
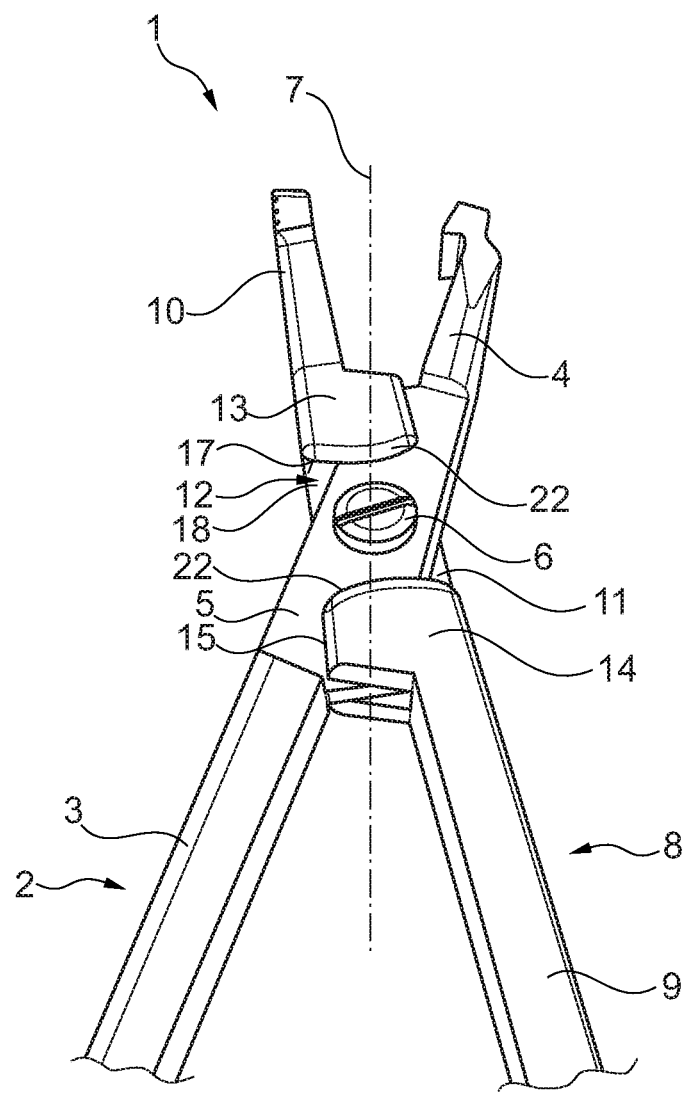
FIG. 2 shows a perspective view of the medical instrument of the first exemplary embodiment in a working and, resp., operating position.

A working and, resp., operating position of the medical instrument 1, as shown in FIG. 2, describes one position or all positions in a predetermined angle (within an angular range) in which the first hand lever 2 is guided relative to the second hand lever 8 by the guide protrusions 13, 14 by means of the bearing portion 5. In the operating position gripping, clamping or cutting of an object such as e.g. human tissue takes place.

The relative pivotability of the two hand levers 2, 8 can be limited by means of a locking mechanism (not shown here) which is provided e.g. at the proximal ends of the respective grip portion 3, 9. This helps to ensure that the operator cannot inadvertently move the medical instrument 1 during operation/use into the mounting and cleaning position.

The guide protrusions 13, 14 have outer edges 15 extending on both sides in the longitudinal direction of the second hand lever 8 which are at least one fifth, preferably one fourth, of the length of the recess 12, which allows for safe guiding of the bearing portion 5 over the entire operating range.

The length of the recess 12 is larger than the width of the first hand lever 2 in the area of the bearing element 6. This helps to ensure easy mounting and, resp., dismounting of the medical instrument 1.

The length of the recess 12 is viewed in the longitudinal direction of the second hand lever 8 and corresponds to the X direction of the coordinate system of FIG. 1. The longitudinal direction of the first hand lever 2 corresponds, in FIG. 1, to the Y direction and the width of the first hand lever 2 extends in the XY plane, which corresponds to the pivoting plane of the medical instrument 1, along the X direction (normal to the Y direction). A thickness of all portions of the first hand lever 2 and of the second hand lever 8 extends in the Z direction of the shown coordinate system.

Both from FIG. 1 and especially from FIG. 2, however, it can be clearly inferred that the thickness of the bearing portion 5 is smaller than the height of a guiding gap 16 formed between an inner surface 17 of the guide protrusions 13, 14 and a surface facing the latter of a so-called connecting arm 19 of the guide portion 11. The surface is an inner surface 18 of the connecting arm 19 and especially in the operating position serves as guide and contact surface 20 facing a contact surface 21 (lower surface in FIG. 1) of the bearing portion 5, wherein said two contact surfaces 20, 21 slidingly contact each other in the operating position.

Each of the guide protrusions 13, 14 has an edge 22 facing the recess 12 (cf. FIG. 2) which edge preferably takes a convex, spherical or rounded shape, as shown, inter alia, in FIG. 1 and FIG. 2.

The work portions 4, 10 may be designed differently, as illustrated in FIG. 1 and FIG. 2, but alternatively they may also show an identical design. The work portions 4, 10, as shown here, are merely exemplified and also different designs of the work portions 4, 10 are possible.

Figure 3:
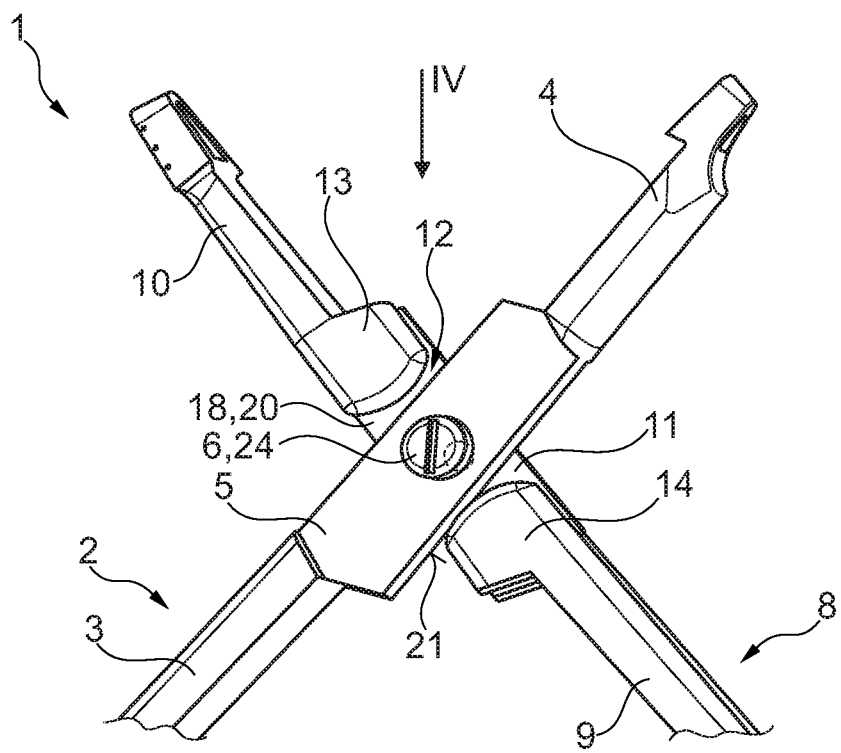
FIG. 3 shows a top view of a second exemplary embodiment of the medical instrument in the mounting and, resp., cleaning position.
Figure 4:
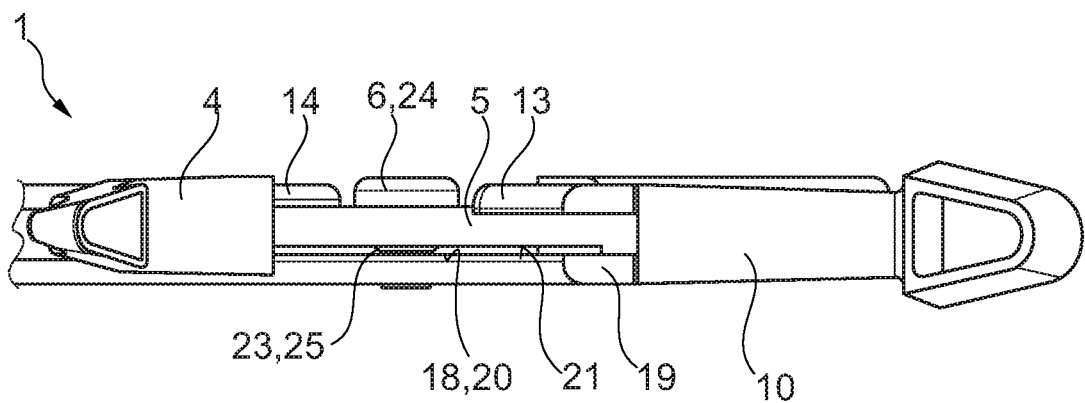
FIG. 4 shows a view from above of the second exemplary embodiment, when viewed in the direction of the arrow IV of FIG. 3.

FIG. 3 and FIG. 4 illustrate a second exemplary embodiment of the medical instrument 1. Said second exemplary embodiment provides that the contact surfaces 20, 21 (cf. FIG. 4) will no longer contact each other as a spacing element 23 for spacing the contact surfaces 20, 21 from each other is positioned therebetween. FIG. 3 illustrates the medical instrument 1 of the second exemplary embodiment in the mounting and cleaning position, with FIG. 3 substantially corresponding to FIG. 1. The difference between the first exemplary embodiment shown in FIG. 1 and the second exemplary embodiment shown in FIG. 3 will become evident only from the view shown in FIG. 4.

In the second exemplary embodiment, just as already in the first illustrated exemplary embodiment, the bearing element 6 is in the form of a screw 24. Alternative embodiments of the bearing element 6 also provide a rivet, for example. However, also further connecting elements are imaginable as bearing element 6, such as e.g. a pin (cf. also FIG. 14 and FIG. 15 in this context).

In FIG. 4 the spacing element 23 is configured as a resistance-forming element in the form of a separate ring 25. As an alternative, the spacing element 23 may as well be configured as an integrally formed ring, e.g. in the form of a peripheral collar or as lands formed on both sides of the bearing element 6. One advantage of the separate component, inter alia, is the easy replaceability of the spacing element 23 which permits, by using different spacing elements, to vary the distance between the guide portion 11 and the bearing portion 5.

Figure 8:
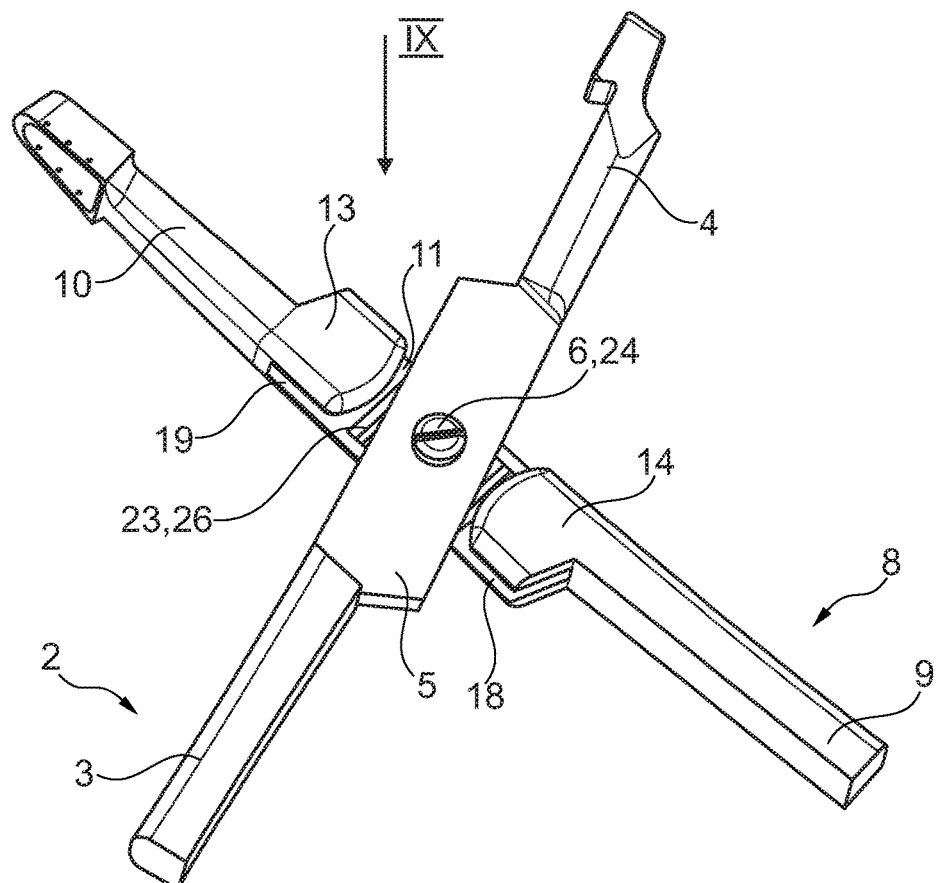
FIG. 8 shows a perspective top view of the medical instrument in a fourth exemplary embodiment in the mounting and, resp., cleaning position.
Figure 9:
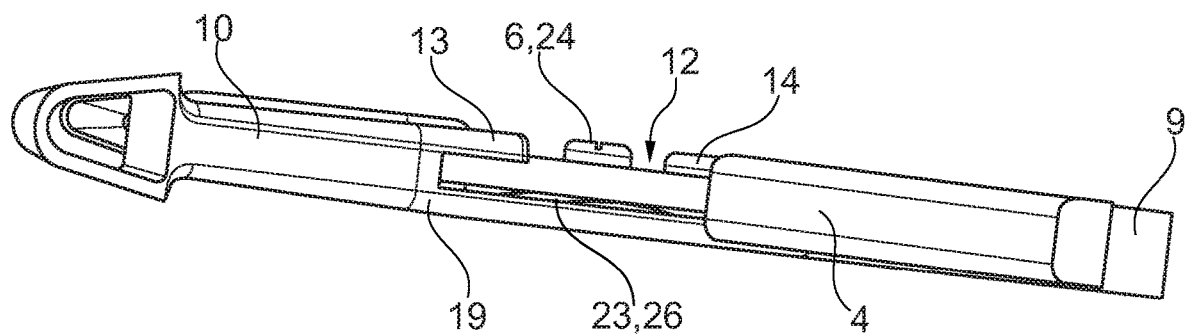
FIG. 9 shows a top view, when viewed along the arrow IX of FIG. 8, of the medical instrument in the fourth exemplary embodiment.

Instead of constituting a resistance, the spacing element 23 may as well be, as exemplified in a fourth embodiment (cf. FIG. 8 and FIG. 9), in the form of a force-applying element such as in the form of a leaf spring 26. Said force-applying elements also include, inter alia, other types of springs such as e.g. a disk spring or a spiral spring, and moreover also magnets, wherein in this case the magnetic repulsion is exploited for spacing the bearing portion 5 and the inner surface 18 of the guide portion 11, or alternatively also a pressure tank is possible. Furthermore, a thermally active element which expands from a particular temperature, for example, and thus results in spacing is also imaginable.

FIGS. 10 to 13 illustrate a fifth exemplary embodiment of the medical instrument 1 in which a spacing element 23 which enables to specifically manually adjust the height (when viewed along/in the direction of the rotation axis 7) of the cleaning gap 27. In this context, FIG. 10 illustrates a top view onto the fifth exemplary embodiment of the medical instrument 1 in the mounting and cleaning position which substantially corresponds to the representations shown in FIG. 1 and FIG. 3.

The spacing element 23 provided in this embodiment is configured so that at the connecting arm 19 (cf. FIG. 11) a spacer sleeve 28 is fastened into which the bearing element 6, which is in the form of a screw 24, can be screwed. I.e. the spacer sleeve 28 in its interior includes a female thread into which the screw 24 can be screwed/turned.

As is evident from FIG. 12 and FIG. 13, in the spacer sleeve 28 there is located a spiral spring 29 which is disposed in a pot 30 formed inside the spacer sleeve 28, the pot 30 having an inner diameter larger than the outer diameter of the female thread. The spiral spring 29 rests, by one of its ends, on the ground/bottom of the pot 30 and is adjacent, by the other end, to the outer face 31 of the connecting arm 19. The height of the cleaning gap 27 can be selectively adjusted via the screwing depth of the bearing element 6 into the female thread of the spacer sleeve 28 and the force transmitted by the bias of the spiral spring 29 that acts on the outer face 31 of the connecting arm 19.

Figure 5:
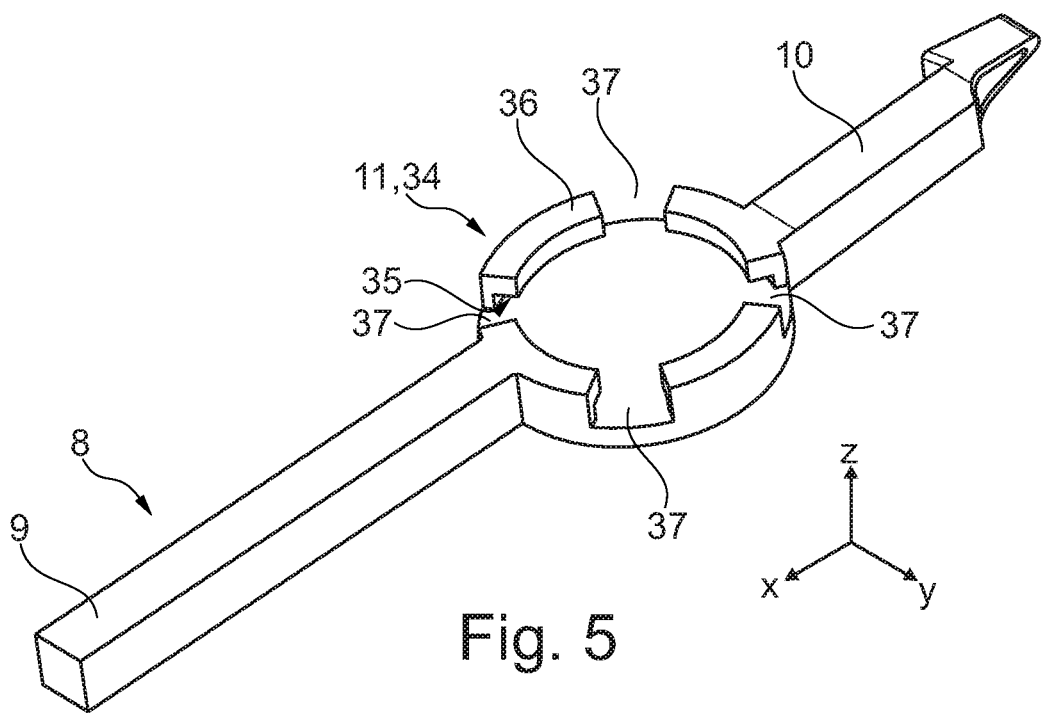
FIG. 5 shows a perspective view of a second hand lever of the medical instrument of a third exemplary embodiment.
Figure 6:
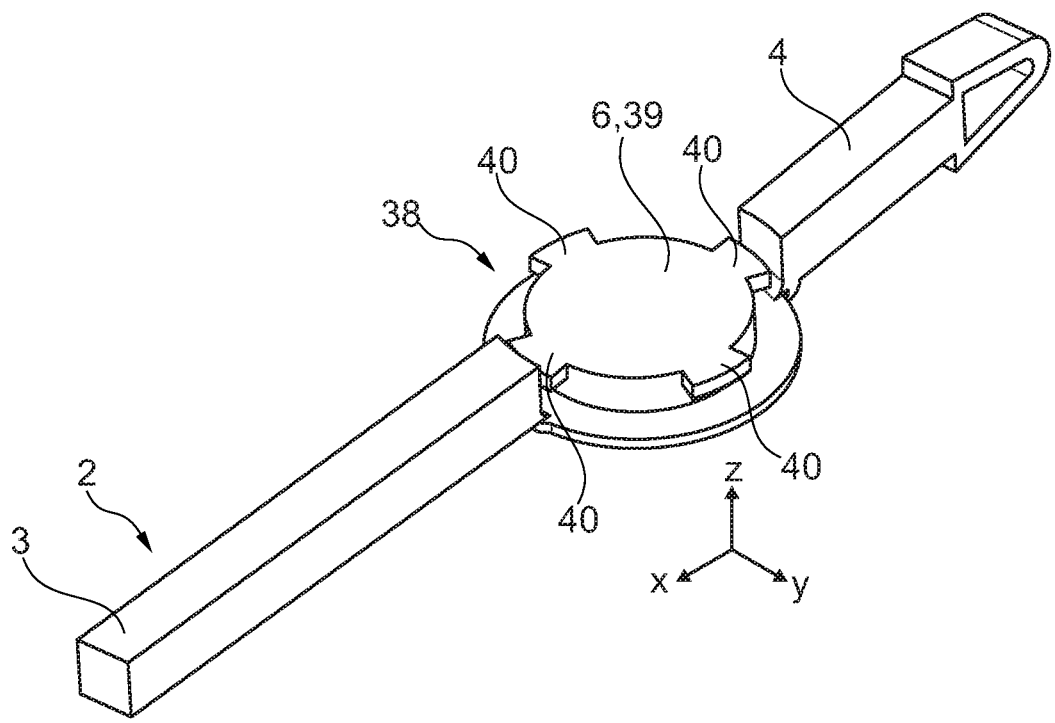
FIG. 6 shows a perspective view of a first hand lever of the medical instrument of the third embodiment.
Figure 7:
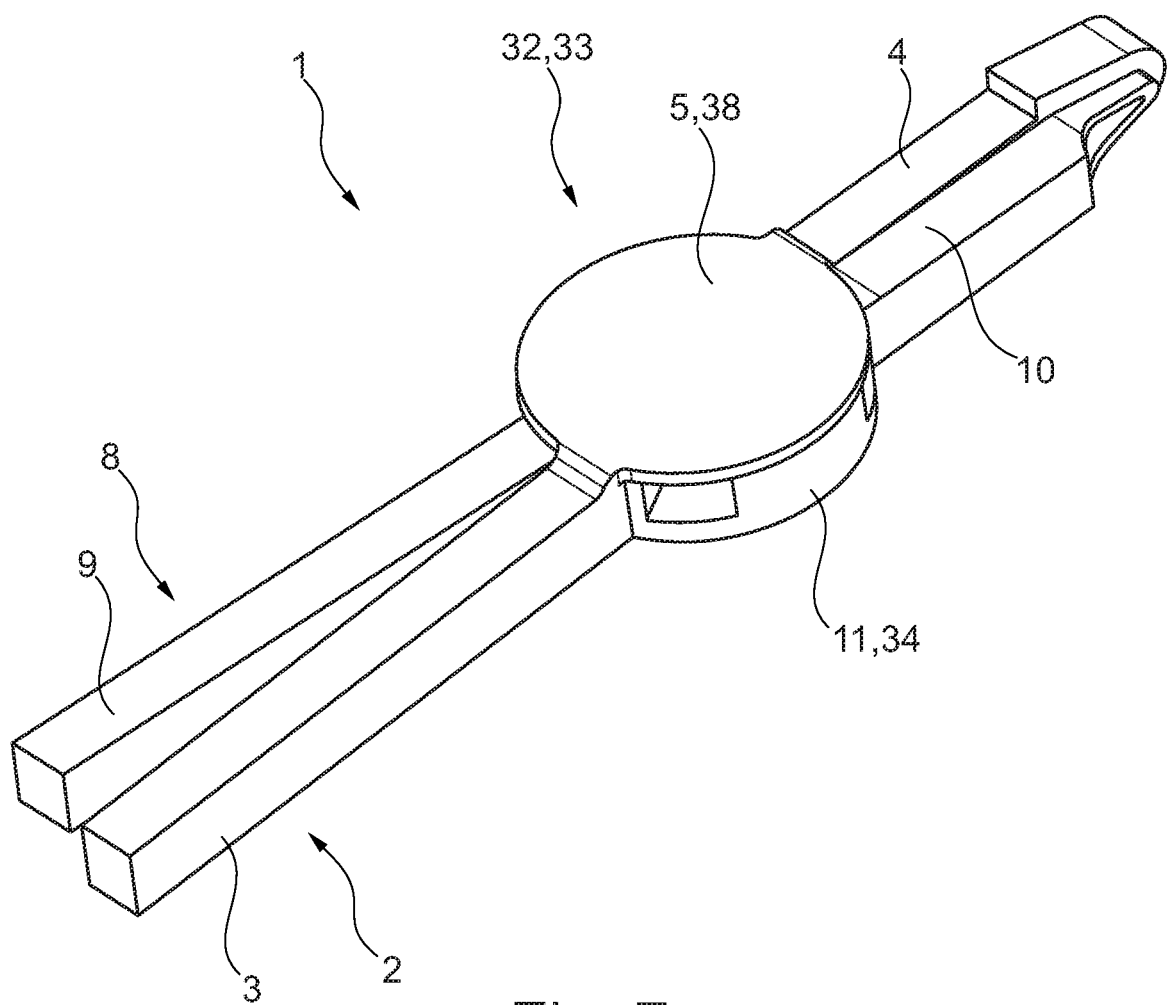
FIG. 7 shows a perspective view of the first hand lever and of the second hand lever of the medical instrument in the third exemplary embodiment in a mounted position.
Figure 14:
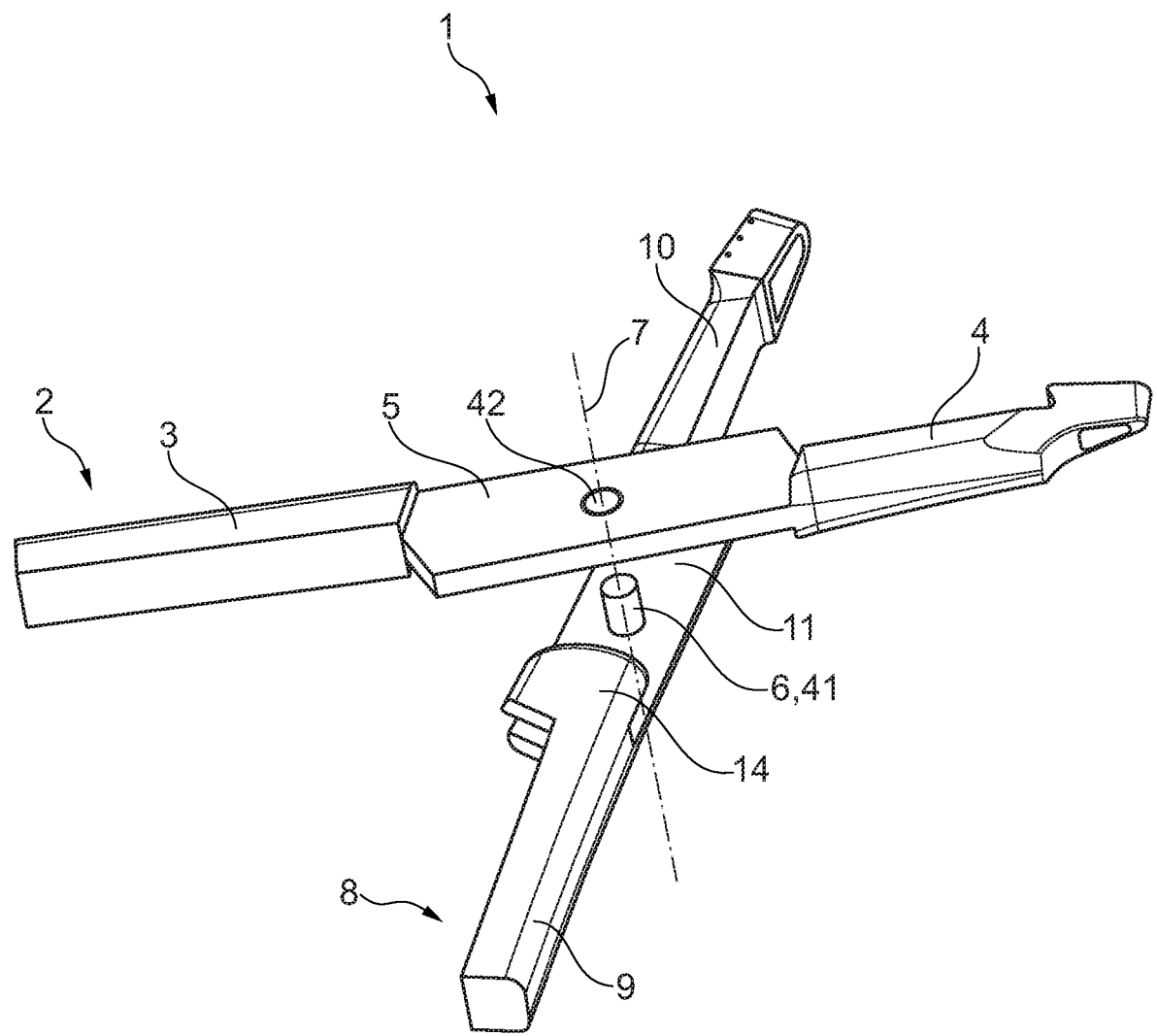
FIG. 14 shows a perspective view of the medical instrument in a sixth exemplary embodiment in a dismounted state.
Figure 15:
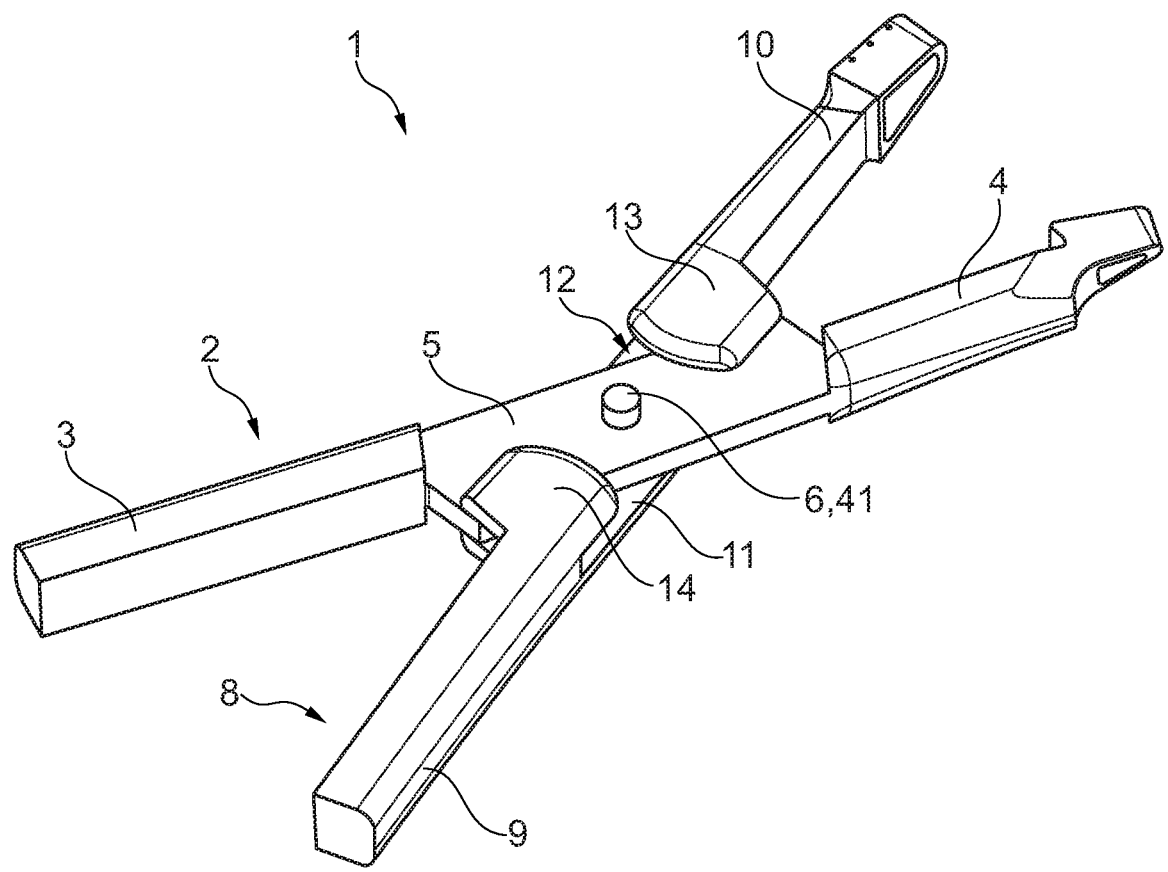
FIG. 15 shows a perspective view of the medical instrument of the sixth exemplary embodiment in the operating position.

FIGS. 5 to 7 as well as FIGS. 14 and 15 illustrate a third and, resp., a sixth exemplary embodiment each of which provides a connection of the hand levers 2, 8 dismountable without the use of tools.

The third exemplary embodiment shown in FIGS. 5 to 7 constitutes a bearing 32 in the form of a bayonet lock 33 (cf. FIG. 7). To this end, e.g. the second hand lever 8 has a guide portion 11 in the form of a guide portion 34 of substantially circular/round shape in the XY plane. The guide portion 34 includes a guiding gap 35 extending in the circumferential direction which is formed by a guide protrusion 36 extending in the circumferential direction, with the guide protrusion 36 extending radially inwardly from an outer circumference of the guide portion 34.

The peripheral guiding gap 35 and, resp., the peripheral guide protrusion 36 are interrupted by at least one, preferably plural (four in FIG. 5) cutouts 37 preferably arranged to be equally spread along the circumferential direction.

The first hand lever 2 shown in FIG. 6 comprises the grip portion 3 and the work portion 4 as already known from the other embodiments. Lying therebetween, the bearing portion 5 is provided in the form of a bearing portion 38 configured in a substantially circular or round shape in the XY plane of FIG. 6, said bearing portion 38 forming the counterpart of the guide portion 34 shown in FIG. 5.

In the bearing portion 38 the bearing element 6 is integrally provided and hereinafter will also be referred to as bearing element 39. The bearing element 39, just as the bearing portion 38, takes a substantially circular shape in the XY plane, extends along a height direction (Z direction in FIG. 6) and has a smaller outer diameter than the bearing portion 38. Said circular bearing element 39 includes at least one, preferably plural or, resp., 2, 3, 4, 5 or 6 (four in FIG. 6) projections or protrusions 40 which extend radially outwardly from an outer circumference of the bearing element 39.

The number of the present projections 40 and the positioning thereof along the periphery corresponds to the number and the positioning of the respective cutouts 37 at the guide portion 34. The guide portion 34 and the bearing portion 38 are adapted to each other so that they are positively engaged and a bayonet lock 33 (cf. FIG. 7) is realized by rotating the two hand levers 2, 8 relative to each other.

The operating position extends over the area defined by the guide protrusions 36. That is to say, the adjusting angle α depends on the number and the positioning of the guide protrusions 36 and, resp., the cutouts 37. In the exemplary embodiment shown in FIG. 5 to FIG. 7, the adjusting angle α is smaller than 90°, for example. However, a larger adjusting angle α (e.g. larger than 90°) can be realized by non-uniform distribution of the projections 40 (and, thus, also non-uniform distribution of the cutouts 37). It is also imaginable as an alternative to design the projections 40 differently so that not each projection will fit into each cutout 37.

The projections 40 shown in this embodiment are trapezoidal. Alternatively, also other geometric shapes such as a pin or a triangular shape etc. are possible which, when interacting with the matching cutouts 37 at the guide portion 34, allow for a bayonet-lock-type connection of the two hand levers 2, 8.

FIG. 14 and FIG. 15 illustrate a sixth exemplary embodiment substantially corresponding to the first embodiment shown in FIG. 1 and FIG. 2, with the difference that merely a pin 41 is provided as bearing element 6. In this case, said pin is formed integrally with the second hand lever 8 and, when mounting the medical instrument 1, in the mounting and cleaning position, is inserted through or into a hole 42 located in the bearing portion 5 of the first hand lever 2. In the operating position the two hand levers 2, 8 are guided relative to each other by means of the guide protrusions 13, 14 (cf. FIG. 15). In the mounting and cleaning position (cf. FIG. 14) the two hand levers 2, 8 can be separated from each other without the use of tools, which corresponds to dismounting the medical instrument 1, e.g. for cleaning and sterilization, without the use of tools.

Alternatively, the bearing element 6 may as well be provided as a separately formed pin, e.g. in the form of a threaded pin, which then can be screwed into a thread provided at the guide portion 11.

LIST OF REFERENCE NUMERALS

1 medical instrument
2 first hand lever
3 grip portion
4 work portion
5 bearing portion
6 bearing element
7 rotation axis
8 second hand lever
9 grip portion
10 work portion
11 guide portion
12 recess
13 guide protrusion
14 guide protrusion
15 outer edge
16 guiding gap
17 inner surface
18 inner surface
19 connecting arm
20 guide and contact surface
21 contact surface
22 edge
23 spacing element
24 screw
25 ring
26 leaf spring
27 cleaning gap
28 spacer sleeve
29 spiral spring
30 pot
31 outer face
32 bearing
33 bayonet lock
34 guide portion
35 guiding gap
36 guide protrusion
37 cutout
38 bearing portion
39 circular bearing element
40 projections
41 pin
42 hole
α adjusting angle

The invention claimed is:

1. A medical instrument comprising:
a first hand lever; and
a second hand lever,
wherein the first hand lever has a manually actuated grip portion at its proximal end, a work portion for gripping, clamping or cutting an object at its distal end and, lying between these, a bearing portion on which a bearing element engages in order to permit pivotability about a rotation axis between the first hand lever and the second hand lever,
wherein the second hand lever has a grip portion at its proximal end, a work portion at its distal end and, lying between these, a guide portion on which the bearing element engages,
wherein the guide portion of the second hand lever has on one side a recess for receiving the bearing portion of the first hand lever such that two guide protrusions located distally and proximally of the recess at least partially cover the bearing portion in an operating position in which gripping, clamping or cutting takes place,
wherein the bearing portion of the first hand lever is configured to be pressed, by a spacing element that provides distance through force or resistance and is in the form of an elastic element, away from the guide portion of the second hand lever in the operating position such that a cleaning gap is formed between the first hand lever and the second hand lever, and
wherein the cleaning gap, when seen in the operating position, extends along an entire length of the guide portion into an area beneath the guide protrusions, viewed in a longitudinal direction of the first hand lever and the second hand lever.

2. The medical instrument according to claim 1, wherein the spacing element is in the form of a separate or integral component.

3. The medical instrument according to claim 1, wherein the spacing element is configured so that a cleaning gap height can be manually adjusted.

4. The medical instrument according to claim 1, wherein the bearing element is in the form of a screw or a rivet.

5. The medical instrument according to claim 1, wherein a cleaning gap height is smaller in the operating position than in a cleaning position.

6. The medical instrument according to claim 5, wherein the cleaning position corresponds to a mounting position of the first hand lever and the second hand lever.

7. The medical instrument according to claim 1, wherein the work portion of the first hand lever and the work portion of the second hand lever are designed identically or differently.

8. A device comprising:
a first hand lever comprising:
a first end,
a second end, and
a bearing portion, located between the first end and the second end, on which a bearing element engages in order to permit pivotability about a rotation axis between the first hand lever and a second hand lever; and
the second hand lever comprising:
a third end,
a fourth end, and
a guide portion, located between the third end and the fourth end, on which the bearing element engages,
wherein the guide portion comprises:
a recess for receiving the bearing portion such that two guide protrusions located distally and proximally of the recess at least partially cover the bearing portion in an operating position in which gripping, clamping or cutting takes place,
wherein the bearing portion is configured to be pressed, by a spacing element that provides distance through force or resistance and is in the form of a separate component, away from the guide portion in the operating position such that a cleaning gap is formed between the first hand lever and the second hand lever, and
wherein the cleaning gap, when seen in the operating position, extends along an entire length of the guide portion into an area beneath the guide protrusions, viewed in a longitudinal direction of the first hand lever and the second hand lever.

9. The device of claim 8, wherein the spacing element is in the form of a spring.

10. The device of claim 8, wherein the spacing element is configured so that a cleaning gap height can be manually adjusted.

11. The device of claim 8, wherein the bearing element is in the form of a screw or a rivet.

12. The device of claim 8, wherein a cleaning gap height is smaller in the operating position than in a cleaning position.

\* \* \* \* \*